(12) United States Patent
Harke et al.

(10) Patent No.: US 10,386,621 B2
(45) Date of Patent: Aug. 20, 2019

(54) METHOD OF USING A HIGH RESOLUTION LASER SCANNING MICROSCOPE AND HIGH RESOLUTION LASER SCANNING MICROSCOPE

(71) Applicant: Abberior Instruments GmbH, Goettingen (DE)

(72) Inventors: Benjamin Harke, Goettingen (DE); Matthias Reuss, Goettingen (DE); Lars Kastrup, Goettingen (DE)

(73) Assignee: ABBERIOR INSTRUMENTS GMBH, Goettingen (DE)

(*) Notice: Subject to any disclaimer, the term of this patent is extended or adjusted under 35 U.S.C. 154(b) by 181 days.

(21) Appl. No.: 15/413,890

(22) Filed: Jan. 24, 2017

(65) Prior Publication Data
US 2017/0212340 A1    Jul. 27, 2017

(30) Foreign Application Priority Data
Jan. 27, 2016   (EP) .................................... 16153001

(51) Int. Cl.
*G02B 21/00*   (2006.01)
*G01N 21/64*   (2006.01)
(Continued)

(52) U.S. Cl.
CPC ..... *G02B 21/0032* (2013.01); *G01N 21/6458* (2013.01); *G02B 21/0076* (2013.01); *G02B 21/16* (2013.01); *G02B 27/58* (2013.01)

(58) Field of Classification Search
CPC  G02B 21/00; G02B 21/0004; G02B 21/0032; G02B 21/0056;
(Continued)

(56) References Cited

U.S. PATENT DOCUMENTS 3,052,152 A * 9/1962 Koester ............. G02B 21/0092
                                                         359/386
7,095,556 B2 * 8/2006 Iketaki ................... G02B 26/08
                                                         250/458.1
(Continued)

FOREIGN PATENT DOCUMENTS

WO    2008/098144 A1   8/2008
WO    2013/067643 A1   5/2013

OTHER PUBLICATIONS

Chen-Kuan Chou et al, "Polarization ellipticity compensation in polarization second-harmonic generation microscopy without specimen rotation," Journal of Biomedical Optics 13(1), 014005, Jan./Feb. 2008.*

(Continued)

*Primary Examiner* — Stephone B Allen
*Assistant Examiner* — James McGee
(74) *Attorney, Agent, or Firm* — Thomas | Horstemeyer, LLP

(57) ABSTRACT

A high resolution laser scanning microscope has beam shaping elements configured to shape a beam of fluorescence inhibiting light which is directed into a back aperture of an objective connected to form an intensity minimum delimited by intensity maxima of the fluorescence inhibiting light in a focus of the objective. A plurality of optical elements including the objective and the beam shaping elements are arranged in a beam path of the beam to the focus. Using the microscope includes removing or exchanging or altering or adding at least one of the optical elements arranged in the beam path of the beam of fluorescence inhibiting light, and compensating a variation of polarization varying properties of the plurality of the optical elements, that is caused by removing or exchanging or altering or (Continued)

adding the at least one optical element, by adapting the beam shaping elements to the variation.

20 Claims, 8 Drawing Sheets

(51) Int. Cl.
*G02B 21/16* (2006.01)
*G02B 27/58* (2006.01)

(58) Field of Classification Search
CPC ........ G02B 21/0068–21/0076; G02B 21/0092; G02B 21/06; G02B 21/16; G02B 21/36–21/362; G02B 27/58; G01N 2201/0635; G01N 21/6458
USPC ................ 359/368, 370–371, 381, 385–390, 359/577–579
See application file for complete search history.

(56) References Cited

U.S. PATENT DOCUMENTS

| | | | |
|---|---|---|---|
| 2011/0069379 A1* | 3/2011 | Becker | G02B 21/248 359/368 |
| 2012/0104279 A1* | 5/2012 | Reuss | G02B 21/0032 250/458.1 |
| 2015/0211986 A1 | 7/2015 | Kuang et al. | |

OTHER PUBLICATIONS

"Knowledge—Objective Lens", Olympus-IMS, found on website at http://www.olympus-ims.com/en/microscope/terms/feature12/, date of search Nov. 2015.
"Objective", Olympus-IMS, Olympus-IMS, found on website at http://www.olympus-lifescience.com/en/objectives/, date of search Nov. 2015.

* cited by examiner

METHOD OF USING A HIGH RESOLUTION LASER SCANNING MICROSCOPE AND HIGH RESOLUTION LASER SCANNING MICROSCOPE

CROSS REFERENCE TO RELATED APPLICATIONS

This present invention claims priority to European Patent Application EP 16 153 001.9 filed on Jan. 27, 2016 and entitled "Verfahren zum Verwenden eines hochauflösenden Laser-Scanning-Mikroskops und hochauflösendes Laser-Scanning-Mikroskop".

FIELD OF THE INVENTION

The present invention relates to a method of using a high resolution laser scanning microscope comprising an objective connector and beam shaping elements. Further, the invention relates to a high resolution laser scanning microscope comprising an objective connector and beam shaping elements. In the method and the laser scanning microscope, the beam shaping elements shape a beam of fluorescence inhibiting light directed into a back aperture of an objective connected to the objective connector, at least with regard to its polarization, to form an intensity minimum of the fluorescence inhibiting light delimited by intensity maxima of the fluorescence inhibiting light in the focus of the objective.

BACKGROUND OF THE INVENTION

In high resolution laser scanning microscopes whose spatial high resolution is achieved by means of a beam of fluorescence inhibiting light, the respective measurement area for which the fluorescence light emitted out of the sample is registered is reduced in size below a diffraction-limited spot of a focused beam of fluorescence excitation in that said spot is superimposed with an intensity distribution of fluorescence inhibiting light which has an intensity minimum delimited by intensity maxima. If the intensity of the fluorescence inhibiting light within the intensity maxima is so high that it drives the fluorescence inhibition up to saturation, whereas the intensity of the fluorescence inhibiting light within the intensity minimum remains so small that the fluorescence inhibiting light does not inhibit the emission of fluorescence light, the registered fluorescence light only origins from the area of the intensity minimum. If the intensity minimum is a zero point of the intensity distribution of the fluorescence inhibiting light formed by interference, the dimensions of the area of the intensity minimum out of which the fluorescence light may still be emitted may be reduced far below the diffraction barrier by increasing the intensity of the fluorescence inhibiting light in the intensity maxima. Here, it is not all-important that the intensity minimum is a real zero point in which the intensity of the fluorescence inhibiting light in fact goes down to zero. Any residual intensity of the fluorescence inhibiting light in the intensity minimum, however, reduces the intensity of the fluorescence light emitted out of the intensity minimum of the fluorescence inhibiting light. Further, a residual intensity of the fluorescence inhibiting light in the intensity minimum delimits the possibility of reducing the area of the intensity minimum by increasing the intensity of the fluorescence inhibiting light. This increase will also increase the residual intensity of the fluorescence inhibiting light in the intensity minimum so that the intensity of the fluorescence light emitted out of the intensity minimum of the fluorescence inhibiting light may even goes down to zero. In such a case no fluorescence light can be registered for measuring a sample in the intensity minimum. Thus, it is of high interest to keep the residual intensity of the fluorescence inhibiting light in the intensity minimum as small as possible, and in an ideal case this intensity is zero.

For the purpose of forming a ring-shaped intensity distribution of fluorescence inhibiting light extending all around the optical axis of the respective objective, which is also designated as a donut, it is known to modulate the wavefronts of the beam of fluorescence inhibiting light in a spiral-shaped way by means of a so-called phase clock. Downstream the phase clock, the angle position of the respective part of the phase front from 0 to $2\pi$ around the optical axis corresponds to a relative phase from 0 to $\lambda$. Here, $\lambda$ is the wavelength of the fluorescence inhibiting light. If the fluorescence inhibiting light of a beam of fluorescence inhibiting light with phase fronts shaped in this way is circularly polarized, particularly with a direction of the circular polarization adapted to the direction of the phase variation, and if the beam of fluorescence inhibiting light is then directed into the back aperture of the objective, a zero point of the intensity of the fluorescence inhibiting light is formed in the focus of the focused beam of fluorescence inhibiting light.

A ring-shaped intensity distribution of the fluorescence inhibiting light extending around the optical axis in the focus of a beam of fluorescence inhibiting light also results if the beam of fluorescence inhibiting light has a linear polarization which rotates about the optical axis in the back aperture of the objective. Such a linear polarization may be achieved by means of a segmented birefringent waveplate in which the individual segments of the waveplate are arranged like pie segments around the optical axis and provide for a linear polarization of the fluorescence inhibiting light which is orthogonal to the radial direction of main extension of the respective segment. Already with four equally sized segments, an essentially ring-shaped intensity distribution of the fluorescence inhibiting light is achieved in the focus of the beam of fluorescence inhibiting light.

For the purpose of also delimiting the intensity minimum of the fluorescence inhibiting light in the direction of the optical axis by means of intensity maxima of the fluorescence inhibiting light, it is known to use a further beam of fluorescence inhibiting light, which is superimposed with the beam of fluorescence inhibiting light forming the ring-shaped intensity distribution of the fluorescence inhibiting light and described above. The wavefronts of the further beam of fluorescence inhibiting light are subdivide into a circle about the optical axis and a ring running around the circle, and a phase step of $\lambda/2$ is provided between the ring and the circle. Here, $\lambda$ is the wavelength of the fluorescence inhibiting light again. With same total intensities of the fluorescence inhibiting light both in the circle and the ring, a zero point of the intensity of the fluorescence inhibiting light is achieved in the focus of the beam of fluorescence inhibiting light, which, in the direction of the optical axis, is delimited by two intensity maxima of the fluorescence inhibiting light. To obtain this equal intensities of the fluorescence inhibiting light in the circle and the ring, a precise adaptation to the back aperture of the objective is required as only those parts of the fluorescence inhibiting light passing through the back aperture of the objective are involved in forming the zero point. At the same time it is of interest to make use of the full back aperture of the objective to narrowly delimit the zero point of the intensity of the fluorescence inhibiting light in the direction of the optical axis by the neighboring intensity maxima of the fluorescence inhibiting light.

The inventors have noticed that high resolution laser scanning microscopes, even with optimally adjusted beam shaping elements, only then provide an intensity minimum of the fluorescence inhibiting light in the focus of the objective, that has the desired zero point or gets close to the desired zero point, when certain objectives are used. They have found out that intensity minima with a residual intensity of the fluorescence inhibiting light close to zero are more often achieved when using objectives which are designated as "suitable for DIC (differential interference contrast) microscopy" by their manufacturers. According to www.olympus-ims.com (Olympus Corporation), these objectives are characterized by reduced lens distortions. According to www.olympus-lifescience.com (Olympus Corporation), the inner tension of an objective UPLFLN-P particularly suited for the DIC microscopy is "reduced to an absolute minimum".

Further, the inventors have noticed that the residual intensity of the fluorescence inhibiting light in the intensity minimum delimited by intensity maxima increases and the intensity of the fluorescence light emitted out of the area of the intensity minimum correspondingly decreases in a high resolution laser scanning microscope, if sample substrates made of certain materials are arranged between the objective and the focus of the objective. Some sample substrates increase the residual intensity of the fluorescence inhibiting light to such an extent that no more fluorescence light emitted out of the area of the intensity minimum is registered.

WO 2008/098144 A1 discloses a device and a method for forming a light beam that when focused will produce an image of a donut-shaped pattern with a zero intensity central point. A beam with uniform or Gaussian profile is directed to a plurality of transparent plates, arranged in pairs on opposite sides of the beam axis. For each pair the plates have a composition in thickness different from each other, and chosen so that the transmitted light has a phase difference of half a wavelength for at least three different wavelengths. An additional plate with a center on the perpendicular to a virtual line connecting the two plates of one of the pairs has a composition and thickness such that the light transmitted through that additional plate has a phase difference of a quarter wavelength with respect to the light transmitted through one of the plates of said pair of plates, at at least one wavelength. This additional plate converts incoming plane polarized light to circularly polarized. This circularly polarized and collimated beam is passed through the plurality of transparent plates converting it to a zero intensity axis beam which is then focused by an objective to a doughnut-shaped pattern in the focus of the objective.

WO 2013/067643 A1 discloses a method and system for improving resolution in laser imaging microscopy. A sample is successively scanned with a first excitation beam having an intensity profile of maximum intensity at a center thereof to obtain a positive image of the sample and a second excitation beam having an intensity profile of minimum intensity at a center thereof and defining a peripheral region of maximum intensity around the center, thereby obtaining a negative image of the sample. Finally, the negative image is subtracted from the positive image to obtain a high-resolution image of the sample. Mode converters for forming the first and second excitation beams may include different optical components or a combination of optical components, including a birefringent waveplate assembly, an electro-optic device, a liquid crystal device and a polarization controller.

There still is a need of a method of using a high resolution laser scanning microscope comprising an objective connector and beam shaping elements for a beam of fluorescence inhibiting light and a corresponding high resolution laser scanning microscope in which, even after exchanging the objective or after removing or exchanging or altering or adding any other of the optical elements arranged in the beam path of the beam of fluorescence inhibiting light to the focus of the objective, the residual intensity of the fluorescence inhibiting light in an intensity minimum in the focus of the objective delimited by intensity maxima still essentially goes down to zero.

SUMMARY OF THE INVENTION

The present invention relates to a method of using a high resolution laser scanning microscope having an objective connector and beam shaping elements. The beam shaping elements is configured to shape a beam of fluorescence inhibiting light which is directed into a back aperture of an objective connected to the objective connector at least with regard to its polarization. The purpose of this beam shaping is to form an intensity minimum of the fluorescence inhibiting light delimited by intensity maxima of the fluorescence inhibiting light in a focus of the objective. A plurality of optical elements which include the objective and the beam shaping elements are arranged in a beam path of the beam of fluorescence inhibiting light to the focus of the objective. The method includes removing or exchanging or altering or adding at least one of the optical elements arranged in the beam path of the beam of fluorescence inhibiting light, and compensating a variation of polarization varying properties of the plurality of the optical elements arranged in the beam path of the beam of fluorescence inhibiting light, that is caused by removing or exchanging or altering or adding the at least one optical element, by adapting the beam shaping elements to the variation.

Further, the present invention relates to a high resolution laser scanning microscope comprising an objective connector and beam shaping elements configured to shape a beam of fluorescence inhibiting light which is directed into a back aperture of an objective connected to the objective connector, at least with regard to its polarization, to form an intensity minimum of the fluorescence inhibiting light delimited by intensity maxima of the fluorescence inhibiting light in a focus of the objective. A plurality of optical elements including the objective and the beam shaping elements are arranged in a beam path of the beam of fluorescence inhibiting light to the focus of the objective. The laser scanning microscope further comprises an adaptation device operatively connected to the beam shaping elements and configured to compensate a variation of polarization varying properties of the plurality of the optical elements arranged in the beam path of the beam of fluorescence inhibiting light, the variation coming along with removing or exchanging or altering or adding at least one the optical element.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
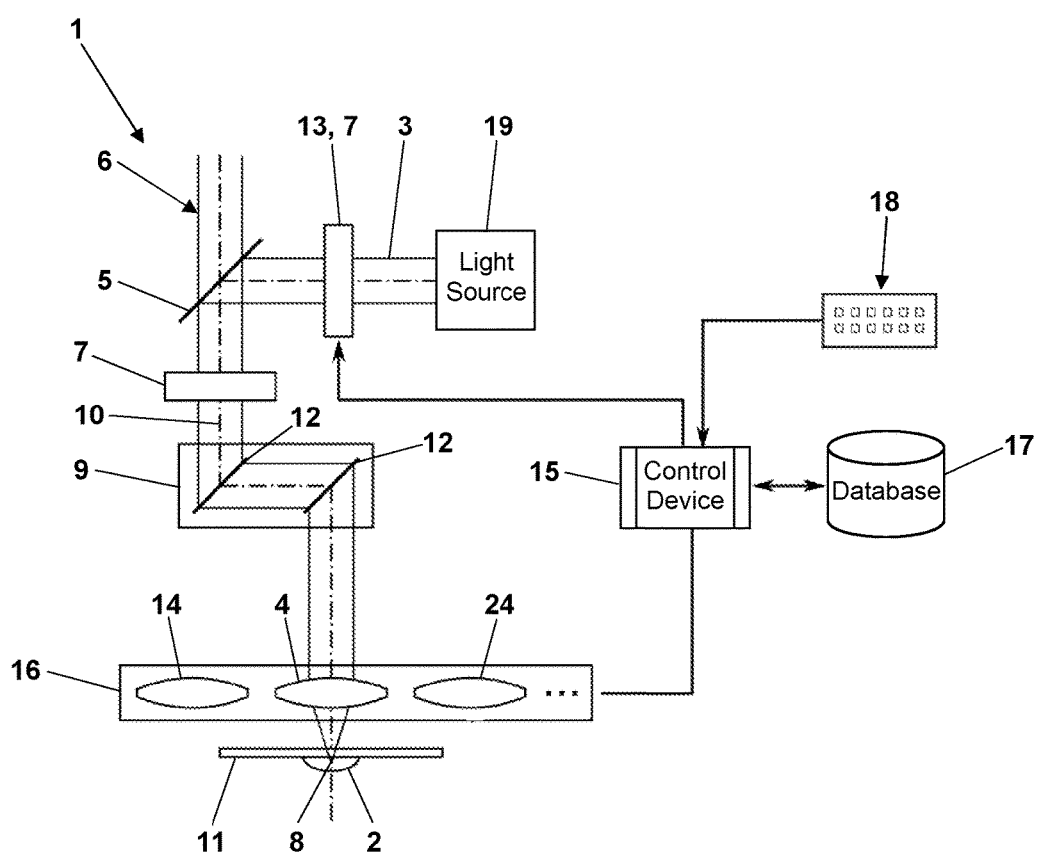
FIG. 1 illustrates an embodiment of a laser scanning microscope of the present invention comprising an objective changer and a light source for a beam of fluorescence inhibiting light.

The method according to the invention starts from the use of a high resolution laser scanning microscope comprising an objective connector and beam shaping elements which shape a beam of fluorescence inhibiting light directed in a back aperture of an objective connected to the objective connector, at least with regard to its polarization, to form an intensity minimum delimited by intensity maxima in a focus of the objective. A plurality of optical elements including the objective and the beam shaping elements are arranged in a beam path of the beam of fluorescence inhibiting light to the focus of the objective. In the use of this high resolution laser scanning microscope, at least one of the optical elements arranged in the beam path of the beam of fluorescence inhibiting light is removed or exchanged or altered or added. The method according to the invention is characterized by compensating a variation of polarization varying properties of the plurality or entirety of the optical elements arranged in the beam path of the beam of fluorescence inhibiting light to the focus of the objective, which is caused by the removal or the exchange or the alteration or the addition of the at least one optical element, by means of adapting the beam shaping elements.

The method according to the invention is based on the finding that different optical elements which are arranged in the beam path of the beam of fluorescence inhibiting light and through which the beam of fluorescence inhibiting light passes or by which it is reflected on its way to the focus of the objective alter the polarization of the beam of fluorescence inhibiting light due to their polarization varying properties in such a way that the preconditions for forming an intensity minimum with an essentially zero residual intensity of the fluorescence inhibiting light in the focus of the objective are not met, although these preconditions should be met due to the adjustment of the beam shaping elements provided for this purpose. Even objectives which are designated by their manufacturers as "polarization maintaining" have such polarization varying properties, for example.

Further, the method according to the invention is based on the finding that these polarization variations of the beam of fluorescence inhibiting light may comparatively easily be compensated by means of the beam shaping elements of the respective laser scanning microscope. Depending on the design of these beam shaping elements, the already present adjusting options of the beam shaping elements may be sufficient, or it is sufficient to make these adjusting options usable. Often, however, it is suitable to create new adjusting options. Even such new adjusting options, however, do not require any high constructive or financial effort.

In a particular embodiment, the method according to the invention is applied in exchanging an objective connected to the objective connector of the laser scanning microscope with another objective. In this embodiment, the beam shaping elements are adapted to the other objective so that, after the exchange, the beam shaping elements upfront compensate a varying polarization alteration or polarization rotation of the beam of fluorescence inhibiting light by the new objective differing from a polarization alteration, particularly a polarization rotation, of the beam of fluorescence inhibiting light by the objective previously connected to the objective connector. Often, the provision of an additional polarization rotation by the beam shaping elements which annuls the polarization rotation of the beam of fluorescence inhibiting light by the other objective is sufficient for this purpose.

When applying the method according to the present invention in exchanging the objective, it is even possible to use objectives which have up to now been regarded as unsuitable for high resolution laser scanning microscopes with beam shaping elements shaping a beam of fluorescence inhibiting light at least with regard to its polarization. The application of the method according to the invention in exchanging the objective provides for a quick adaptation of the laser scanning microscope to the respective objective. This adaptation may as such, i.e. without any readjustment, be sufficient to use the laser scanning microscope with the new objective for high resolution microscopy.

In a further particular embodiment, the method according to the invention is applied in using the high resolution laser scanning microscope in combination with different sample substrates arranged between the objective and the focus of the objective. Here, the beam shaping elements are adapted to the sample substrate made of polarization varying material such that they upfront compensate for a polarization variation, particularly a polarization rotation of the beam of fluorescence inhibiting light by means of the respective sample substrate. Also for this purpose, the adjustment of an additional polarization rotation by the beam shaping elements which annuls the polarization rotation of the beam of fluorescence inhibiting light by the respective sample substrate is often sufficient.

Besides the exchange of the objective or the change between different sample substrates, the method according to the invention may also be applied when removing or exchanging or altering or adding other optical elements out of or in or into the beam path of the beam of fluorescence inhibiting light to the focus of the objective. Removing or exchanging or adding a dichroic mirror out of or in or into the beam path of the beam of fluorescence inhibiting light, which—without compensation—would significantly affect the polarization of the beam of fluorescence inhibiting light and thus the quality of the intensity minimum in the focus of the objective due to the polarization varying properties of the dichroic mirror, belong to this aspect.

It is a lesser, or it may even be no aspect of the present invention to compensate a variation of the polarization of the beam of fluorescence inhibiting light which is due to removing or exchanging or altering or adding optical elements which are especially provided in the beam path for varying the polarization of the beam of fluorescence inhibiting light. When using a high resolution laser scanning microscope, it is, however, not usual to remove or exchange or add optical elements which are particularly provided for polarization alteration from the or in the or into the beam path of the beam of fluorescence inhibiting light. Optical elements particularly provided for polarization variation are, for example, waveplates.

Further, it is a lesser, or it may even be no aspect of the present invention to compensate a variation of the polarization of the beam of fluorescence inhibiting light which results from a pure fine adjustment or readjustment of an optical element in the beam path of the beam of fluorescence inhibiting light. Instead, the step of altering an optical element in the beam path of the beam of fluorescence inhibiting light particularly means the basic adjustment of the optical element taking place during exchange or addition which may also be regarded as a part of the exchange or addition.

When adapting the beam shaping elements to the objective, the sample substrate or any other optical element with polarization varying properties in the beam path of the beam of fluorescence inhibiting light, the beam shaping elements may be adjusted to an adjustment predetermined by an identifier of the respective optical element. This means that, in principle, no fine adjustment or readjustment of the laser scanning microscope to the respective optical element is needed, if the removed or exchanged or altered or added optical element is known. Instead, it is essentially sufficient to adjust the beam shaping elements to an adjustment predetermined by the identifier of the optical element.

The identifier of the respective optical elements may be read in when removing or exchanging or altering or adding the optical element, and the adjustment predetermined by the identifier of the removed or exchanged or altered or added optical element may be read in from a database using the identifier. This database may be provided in the laser scanning microscope or a computer connected thereto. Alternatively, it may be provided externally. In this case, the database may, for example, be accessed via the internet. The identifier may be be read in directly from the optical element or from a unit directly connected to or otherwise coupled to the optical element. For example, the identifier may be the place or location of a respective objective in an objective changer or it may be stored for this place or location in the laser scanning microscope.

Generally, the optimum adjustment of the beam shaping elements may, however, also be found by purposefully varying the adjustment of the beam shaping elements. Thus, in the adaptation after removing or exchanging or altering or adding the optical element, the adjustment of the beam shaping elements may be varied with the goal of maximizing a fluorescence light intensity registered for the area of the intensity minimum and/or minimizing a residual intensity of the fluorescence inhibiting light registered for the area of the intensity minimum. This approach is based on the fact that only if an intensity minimum with a low residual intensity of the fluorescence inhibiting light is formed an appreciable yield of fluorescence light out of the area of the intensity minimum is achieved and that this yield is the higher the closer the intensity minimum gets to the desired zero point. Such a purposeful variation of the adjustment of the beam shaping element may be effected in a fully automatic way according to so-called fuzzy logic, for example.

The adaptation of the beam shaping elements to the respective objective, the respective sample substrate or the other optical element with the polarization varying or altering properties may include one or more of the following measures:

arranging at least one further beam shaping element in the beam path of the beam of fluorescence inhibiting light, removing at least one of the beam shaping elements from the beam path of the beam of fluorescence inhibiting light, exchanging at least one of the beam shaping elements arranged in the beam path of the beam of fluorescence inhibiting light, and readjusting at least one of the beam shaping elements arranged in the beam path of the beam of fluorescence inhibiting light.

Readjusting the at least one of the beam shaping elements may include rotating and/or tilting and/or adjusting a phase delay of at least one of two birefringent optical elements of the beam shaping elements. Thus, for example, an output side $\lambda/4$ plate of the beam shaping elements which serves for circularly polarizing the beam of fluorescence inhibiting light may be rotated and/or tilted.

In another particular embodiment, a $\lambda/2$ plate is arranged in front of an output side $\lambda/4$ plate of the beam shaping elements, the $\lambda/2$ plate having a certain rotation position with regard to the output side $\lambda/4$ plate. Here, the $\lambda/4$ plate also serves for circularly polarizing the beam of fluorescence inhibiting light. In a certain rotation position, the upstream $\lambda/2$ plate may prevent a complete circular polarization of the fluorescence inhibiting light by the $\lambda/4$ plate. A polarization rotation by the downstream objective, for example, may nevertheless result in a complete circular polarization of the beam of fluorescence inhibiting light in the focus of the objective. Thus, the rotation position of the $\lambda/2$ plate arranged upstream the $\lambda/4$ plate may be adapted to the respective optical element which is removed out of the beam path of the beam of fluorescence inhibiting light or added thereto or exchanged therein to compensate the variation of the polarization by the respective optical element. Particularly, the $\lambda/2$ plate may be replaced by a $\lambda/2$ plate having the appropriate rotation position by means of a rotary disc arranged upstream the $\lambda/4$ plate and carrying a separate $\lambda/2$ plate for each possible combination of optical elements, for example.

In addition to rotating the upstream $\lambda/2$ plate with regard to the output side $\lambda/4$ plate of the beam shaping elements, the output side $\lambda/4$ plate may also be rotated. Then, the adjustment of the beam shaping elements dependent in the respective optical element having the polarization varying properties includes setting both two rotation angles are.

Further, an output side electro-optical device or an electro-optical device arranged upstream an output side $\lambda/4$ plate of the beam shaping elements may be operated to provide the desired polarization rotation.

If the objective is exchanged in the method according to the invention, a shape of the wavefronts achieved with the beam shaping elements may additionally be adapted. Particularly, the shape of the wavefronts may be adapted to the back aperture of the respective objective. This adaptation of the shape of the wavefronts of the beam of fluorescence inhibiting light to the back aperture of the respective objective by means of the beam shaping elements is also an invention by its own which may be used separately from the compensation of the polarization variation or polarization rotation by the objective.

Most efficiently, the shape of the wavefronts of the beam of fluorescence inhibiting light is adapted to the respective objective by means of differently operating at least one spatial light modulator or adaptive mirror. The adaptive mirror may have a plurality of micromirrors arranged side by side in two lateral directions and separately controllable in longitudinal or depth direction.

A high resolution laser scanning microscope according to the present invention comprises an objective connector and beam shaping elements which are configured to shape a beam of fluorescence inhibiting light directed into a back aperture of an objective connected to the objective connector. The beam shaping elements shape the beam of fluorescence inhibiting light, at least with regard to its polarization, to form an intensity minimum delimited by intensity maxima in a focus of the objective. A plurality of optical elements including the objective and the beam shaping elements are arranged in the beam path of the beam of fluorescence inhibiting light to the focus of the objective. Further, the high resolution laser scanning microscope according to the present invention comprises an adaptation device operatively connected to the beam shaping elements. The adaption device is configured to, when removing or exchanging or altering or adding at least one of the optical elements arranged in the beam of fluorescence inhibiting light, compensate a variation of polarization varying properties of the plurality or entirety of the optical elements arranged in the beam path of the beam of fluorescence inhibiting light caused by the removal or the exchange or the alteration or the addition of the respective at least one optical element.

A read in device and/or an input device for an identifier of a removed or exchanged or altered or added optical element may be provided at the laser scanning microscope according to the invention. Particularly, the read in device may be provided at the objective connector of the laser scanning microscope and, for example, monitor the present setting or active position of an objective changer of the laser scanning microscope, that holds a plurality of objectives in different positions. Which objective is at which position of the objective changer may be stored in the laser scanning microscope. Additionally, the respective adjustment of the adaptation device to the respective objective may be stored in the laser scanning microscope, or it may be read in from an external database. In each case, the adaptation device may be configured to implement an adjustment of the beam shaping elements predetermined by the identifier of the respective removed or exchanged or altered or added optical element and causing a polarization rotation of the fluorescence inhibiting light.

The adaptation device of the laser scanning microscope according to the invention may include at least two birefringent optical elements, at least one of which being rotatable or tiltable or adjustable with regard to its phase delay by means of the adaption device. The birefringent optical elements may be selected from waveplates, $\lambda/2$ and $\lambda/4$ plates, liquid crystal devices (LCD) and liquid crystal polymers (LCP), and electro-optical (EO) elements.

At least one of the birefringent optical elements may be rotatable or tiltable about at least two space axes by the adaptation device. The space axes are preferably orthogonal, at least they are non-parallel.

At least one of the birefringent optical elements may be rotatable or tiltable or adjustable with regard to its phase delay by means of the adaptation device electrically or by means of a motor in that, for example, an electro-optical device or a servomotor for rotating or tilting a waveplate of the beam shaping elements is provided.

In one embodiment, the beam shaping elements may include an active optical substance which may be activated by the adaptation device by means of applying an electrical field, for example.

Further, the beam shaping elements may include at least one spatial light modulator or adaptive mirror for shaping wavefronts of the fluorescence inhibiting light which is operated by the adaptation device to adapt the shape of the wavefronts to the back aperture of the respective objective by differently operating the spatial light modulator or adaptive mirror.

Now referring in greater detail to the drawings, a laser scanning microscope 1 schematically depicted in FIG. 1 serves for examining or measuring a sample 2 which is scanned with a light intensity distribution. The light intensity distribution includes a beam 3 of fluorescence inhibiting light. Often, the light intensity distribution additionally includes a beam of excitation light, which, together with the beam 3 of fluorescence inhibiting light, is focused by an objective 4 into the sample 2. As the present invention particularly relates to the beam 3 of fluorescence inhibiting light, only this beam 3 path is depicted here. The beam 3 of fluorescence inhibiting light is provided by a light source 19 and coupled into a main beam path 6 of the laser scanning microscope 1 by means of a dichroic mirror 5. Beam shaping elements 7 adjust at least the polarization of the beam 3 of fluorescence inhibiting light in such a way that an intensity distribution of the fluorescence inhibiting light in a focus 8 of the objective 4 comprises an intensity minimum having an as low as possible residual intensity of fluorescence inhibiting light and surrounded by intensity maxima. With this intensity minimum, the sample 2 is scanned. For this purpose, the focus 8 of the objective 4 is moved by means of a scanner 9 which translationally moves the beam 3 of fluorescence inhibiting light. Ideal conditions for forming an intensity minimum with minimum residual intensity of the fluorescence inhibiting light in the focus 8 should, for example, be present if the beam shaping elements 7 provide a spiral-shaped course of the wavefronts of the beam 3 of fluorescence inhibiting light about the optical axis 10 and circularly polarize the beam 3 of fluorescence inhibiting light. For the latter purpose, the beam shaping elements may include a $\lambda/4$ plate arranged in front of the objective 4. Even if these conditions are fulfilled, however, the desired intensity minimum with low residual intensity of the fluorescence inhibiting light in the focus 8 is often not achieved. According to the findings of the inventors of the present invention, this is due to the fact that the objective 4, any sample substrate arranged in front of the sample 2 or any other optical element 12 arranged in the beam path of the beam 3 of fluorescence inhibiting light may and will have polarization varying properties which prevent the desired polarization of the beam of fluorescence inhibiting light in the focus 8. The resulting polarization variation is corrected by an adaptation device 13, which is connected to the beam shaping elements 7 and which acts upon the polarization of the beam 3 of fluorescence inhibiting light by the beam shaping elements 7 in such a way that any unwanted variations of the polarization of the beam 3 of fluorescence inhibiting light, like for example caused by the objective 4, the sample substrate 11 or any other optical element 12 arranged in the beam path of the beam 3 of fluorescence inhibiting light, are compensated. If, for example, several different objectives 4, 14, 24 or different sample substrates 11 are used, the actual undesired variation of the polarization of the beam 3 of fluorescence inhibiting light is dependent on the objective 4, 14 or 24 or sample substrates 11 actually used. Correspondingly, the adaptation device 13 has to adjusted the beam shaping elements 7 differently with different objectives 4, 14, 24 and sample substrates 11. For this purpose, a control device 15 is provided. The control device 15 monitors the setting of an objective changer 16 serving as an objective connector of the laser scanning microscope 1. Particularly, the control device 15 monitors which objective 4, 14, 24 is actually used. Depending on the objective 4, 14, 24 actually used, the control device 15 sets the adaptation device 13. The control device 15 may request the suitable setting of the adaptation device 13 from a database 17. The database 17 may be provided locally or it may be accessible via the internet. When using different sample substrates 11, an identifier of the respective sample substrate 11 has to be entered into the control device 15 via an input device 18, for example, so that the control device 15 may provide the suitable setting of the adaptation device 13 for compensating the variation of the polarization caused by the respective sample substrate 11 by means of the beam shaping elements 7.

Figure 2:
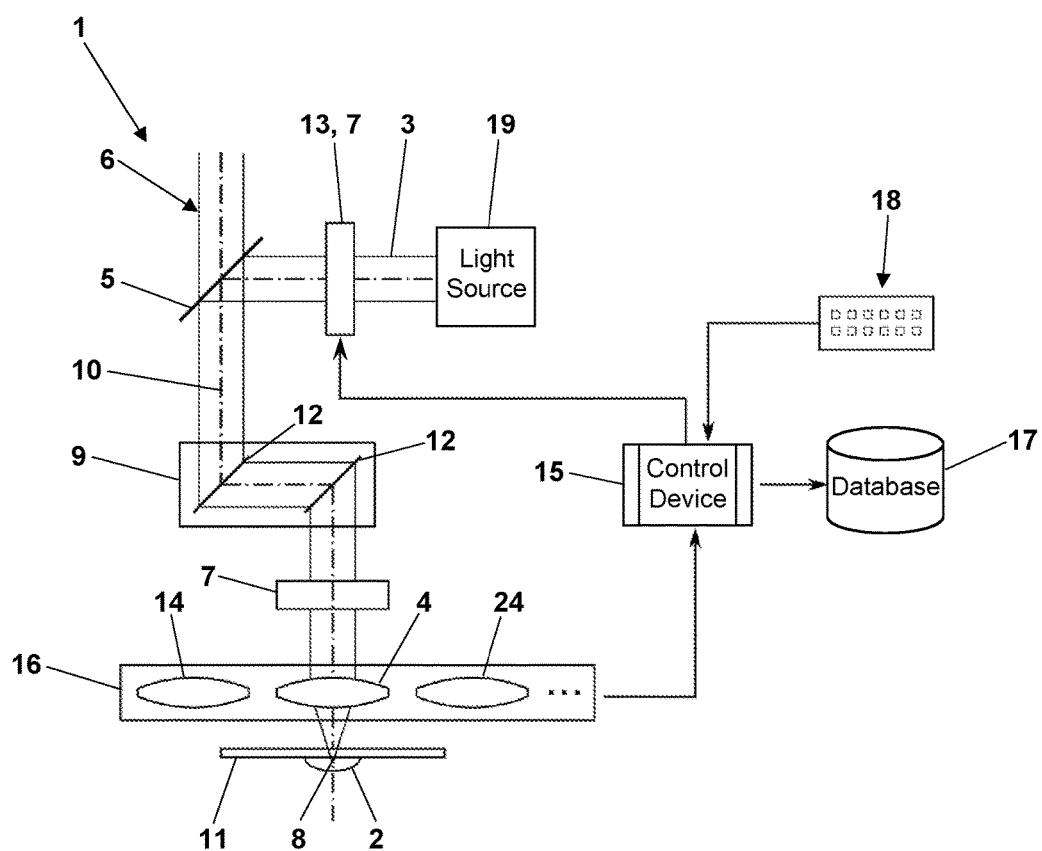
FIG. 2 illustrates a variant of the embodiment of the laser scanning microscope of the present invention according to FIG. 1.

Whereas in the embodiment of the laser scanning microscope 1 according to FIG. 1 all beam shaping elements 7, from the point of view of the light source 19, are arranged upstream or in front of the scanner 9, some of the beam shaping elements 7, like for example a $\lambda/4$ plate, are arranged behind or downstream the scanner 9 in the embodiment of the laser scanning microscope 1 according to FIG. 2.

Figure 3:
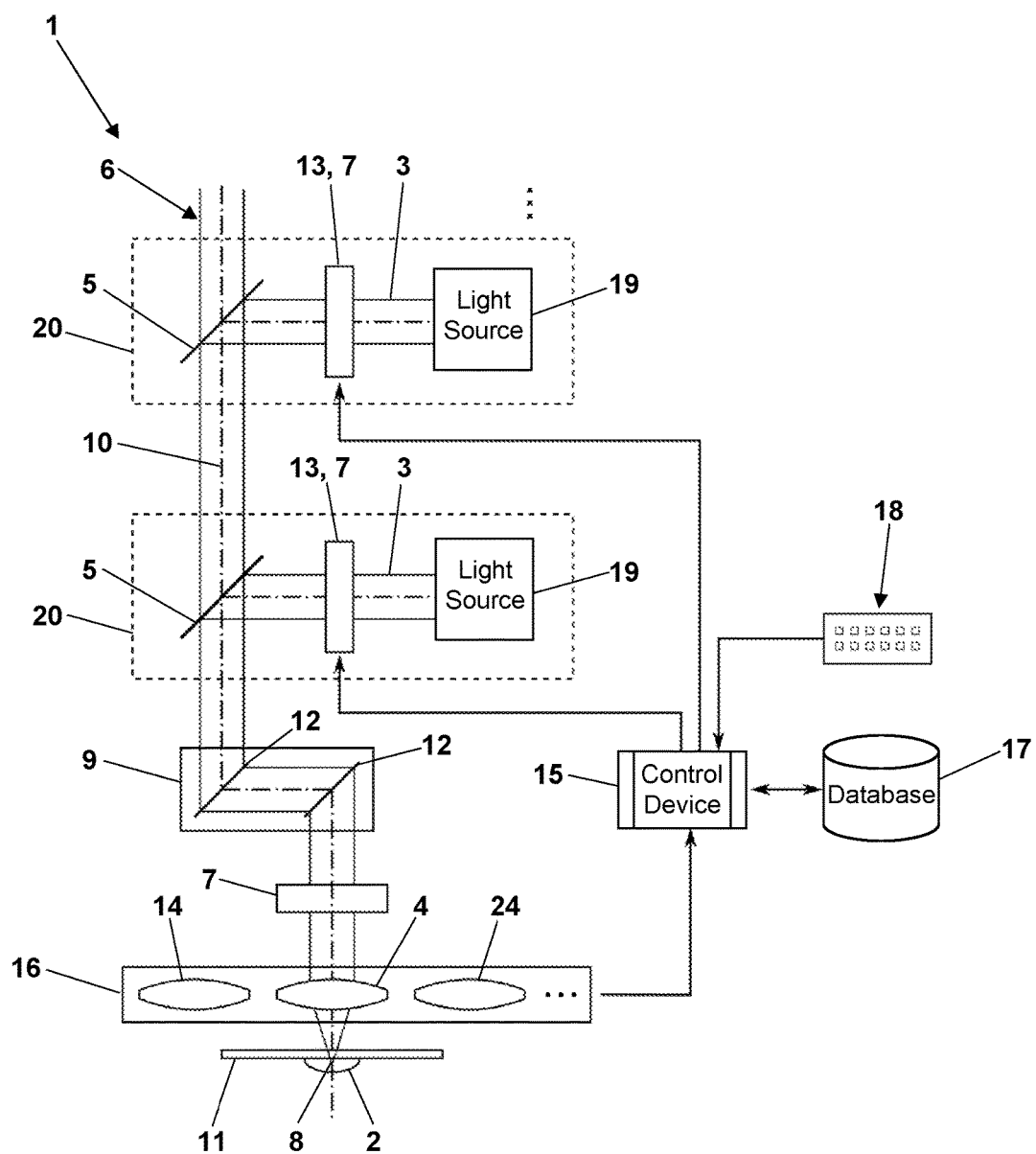
FIG. 3 illustrates an embodiment of the laser scanning microscope of the present invention comprising an objective changer and two light sources for a beam of fluorescence inhibiting light.

In the embodiment of the laser scanning microscope 1 according to FIG. 3, like in FIG. 2, some of the beam shaping elements 7 are arranged between the scanner 9 and the objective 4. According to FIG. 3, a further light source 19 is provided for providing a further component of the beam 3 of fluorescence inhibiting light. Together with a further dichroic mirror 5 and a further adaptation device 13, the further light source 19 forms a further adjustable illumination unit 20. One of the illumination units 20 may provide a component of the beam 3 of fluorescence inhibiting light which delimits the intensity minimum in the focus 8 by intensity maxima in z-direction of the optical axis 10, whereas the other illumination unit 20 provides a component of the beam 3 of fluorescence inhibiting light delimiting the intensity minimum in the focus 8 by intensity maxima in x- and y-directions orthogonal to the optical axis 10. Alternatively, one of the illumination units 20 may provide on component of the beam 3 of fluorescence inhibiting light having one wavelength, whereas the other illumination unit 20 provides another component of the beam 3 of fluorescence inhibiting light having another wavelength. The two wavelengths of the two components may, for example, be adapted to two different fluorophores within the sample 2 which have different absorption spectra for fluorescence inhibiting light. Due to the fact that both illumination units 20 have a separate adaptation device 13 for the respective component of the beam 3 of fluorescence inhibiting light, the polarizations of the two components may in any case be optimized by the control unit 15 independently of each other to achieve the desired intensity minimum with low residual intensity of the fluorescence inhibiting light in the focus 8.

Figure 4:
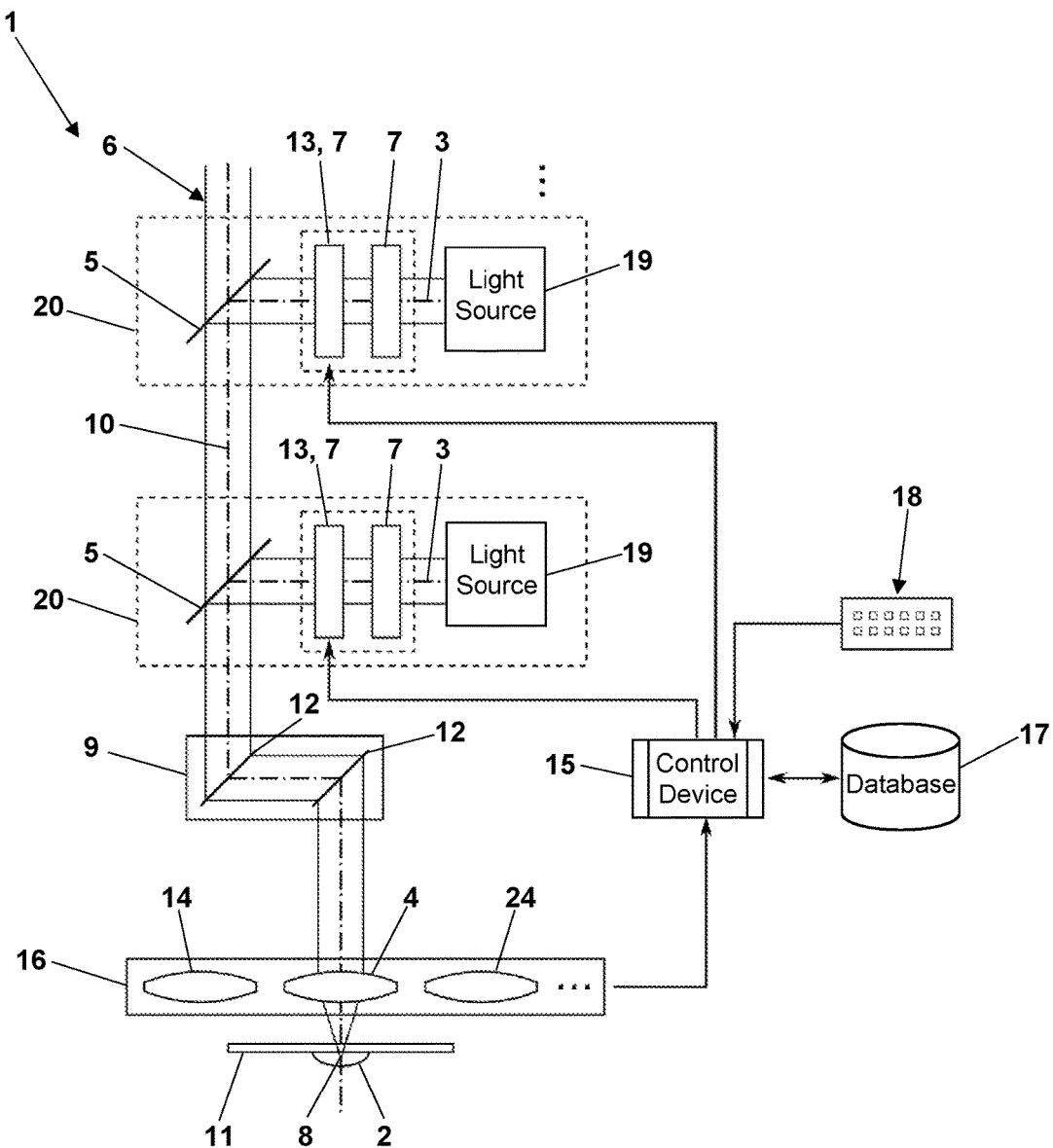
FIG. 4 illustrates a variant of the embodiment of the laser scanning microscope of the present invention according to FIG. 3.

In the embodiment of the laser scanning microscope 1 according to FIG. 4 the beam shaping elements 7 are distributed over both illumination units 20 in such a way that each illumination unit 20 has own beam shaping elements 7 for the respective component of the beam 3 of fluorescence inhibiting light. By the respective adaptation device 13, the polarization of the respective component of the beam 3 of fluorescence inhibiting light is adjusted in adaptation to the respective objective 4, 14, 24 and the respective sample substrate 11 such that the desired intensity minimum with low residual intensity of the fluorescence inhibiting light is formed in the focus 8 of the respective objective.

Figure 5:
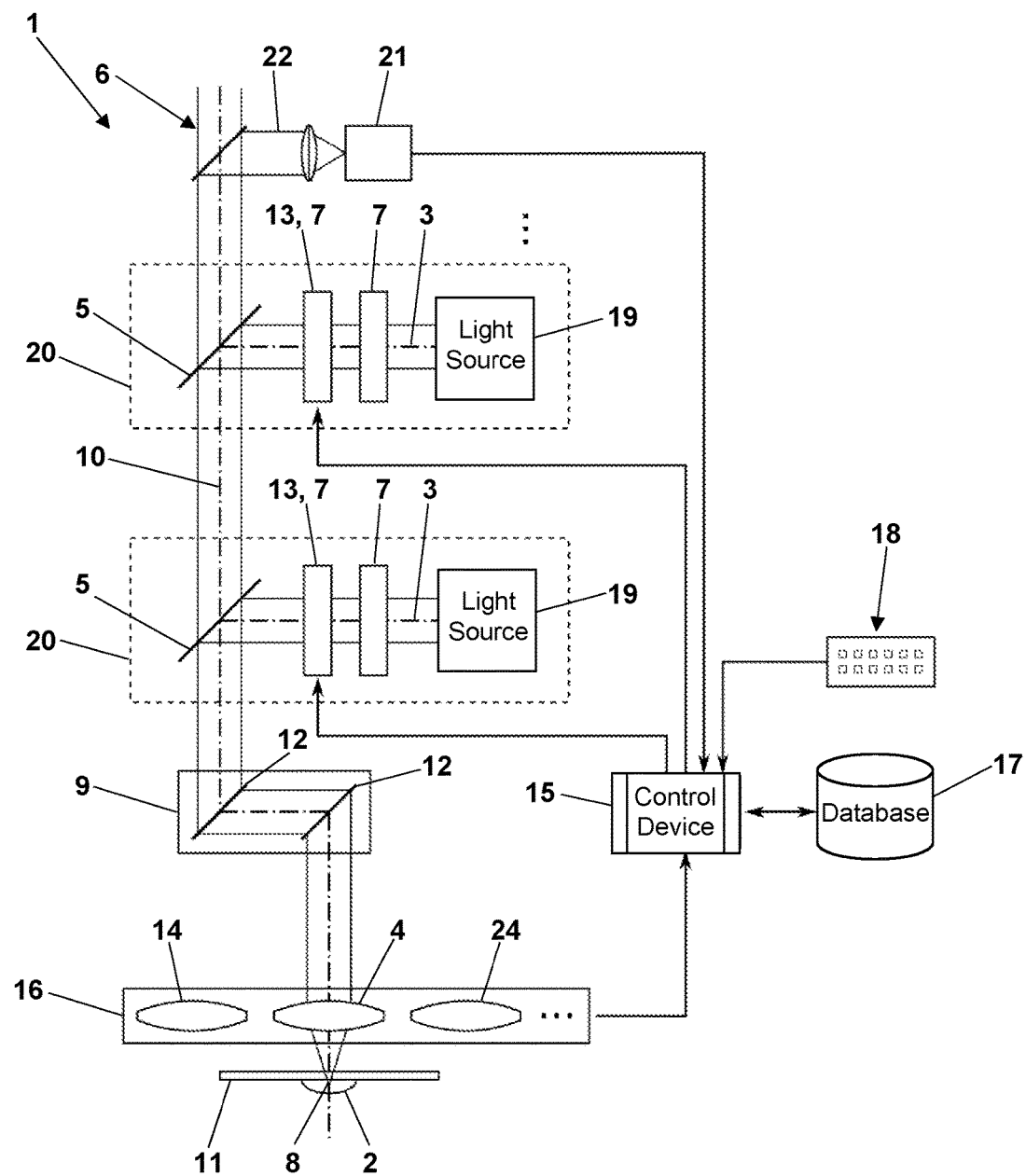
FIG. 5 illustrates a variant of the embodiment of the laser scanning microscope of the present invention according to FIG. 4, which comprises an additional detector.

FIG. 5, in addition to FIG. 4, shows a detector 21 confocally arranged with regard to the focus 8 and detecting fluorescence light 22 emitted out of the sample 2. The fluorescence light 22 is coupled out of the main beam path 6 of the laser scanning microscope 1 via which fluorescence excitation light 23 is directed to the sample 2. A signal of the detector 21 is used for fine adjusting the adaptation device 13 in that its setting is varied until—with otherwise constant parameters—the intensity of the fluorescence light 22 is maximized. This means that the residual intensity of the fluorescence inhibiting light in the focus 8 is minimized.

Figure 6:
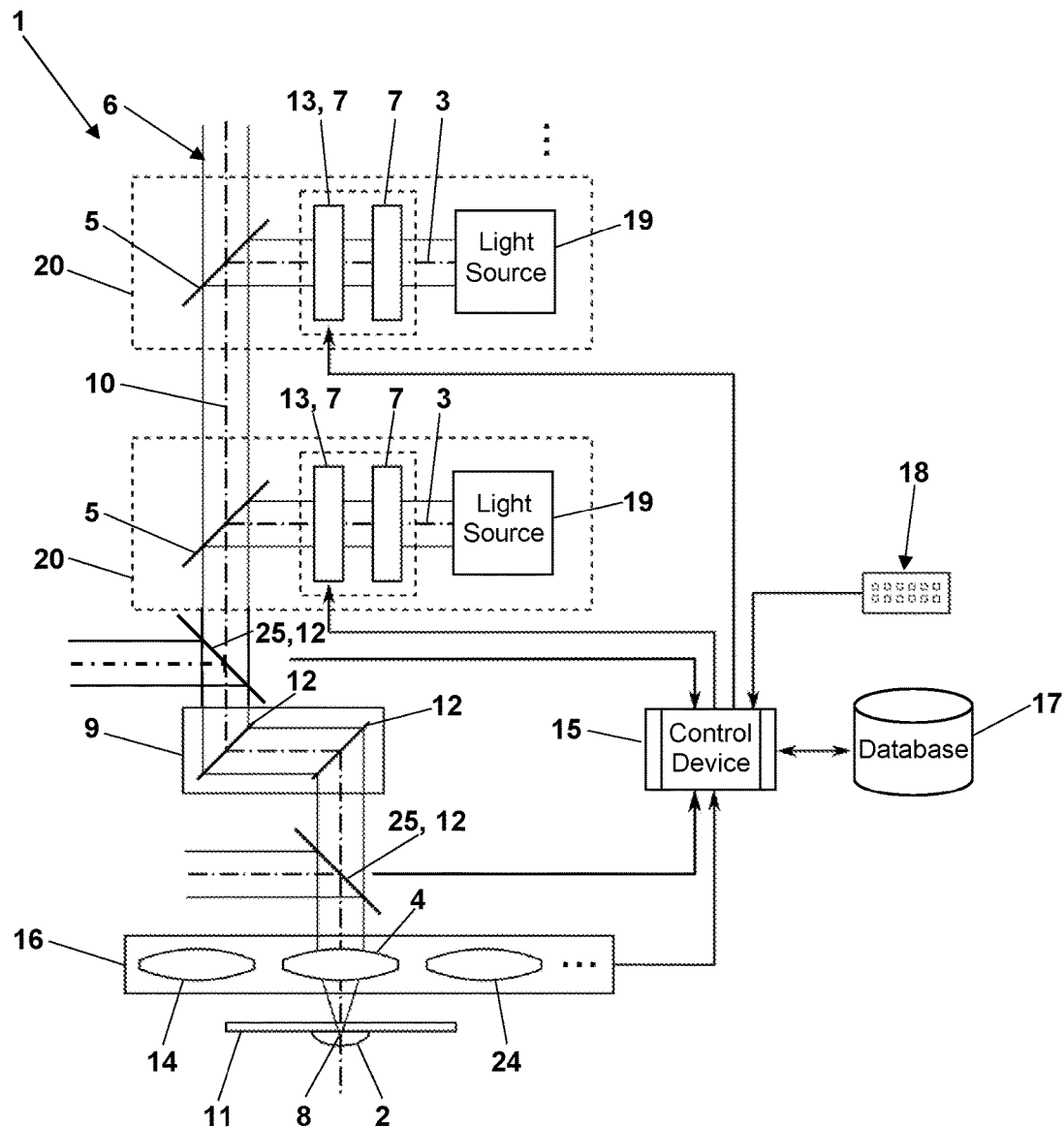
FIG. 6 illustrates a variant of the embodiment of the laser scanning microscope of the present invention according to FIG. 4, which comprises an optional dichroic mirror.

FIG. 6 illustrates how, in the arrangement according to FIG. 4, an optional dichroic mirror 25 as a further optical element 12 may be arranged at various points in the beam path of the beam 3 of fluorescence inhibiting light to couple out certain components of the fluorescence light 22 from the sample 2 towards a detector, for example. By means of setting the adaptation device 13 by the control device 15, the effects of the dichroic mirror 25 on the polarization of the beam 3 of fluorescence inhibiting light in the focus 8 are compensated. The effects of the dichroic mirror 25 on the polarization of the beam 3 of fluorescence inhibiting light and thus also their compensation depend both on the dichroic mirror 25 as such and on the angles under which it is oriented with regard to the optical axis 10.

Figure 7:
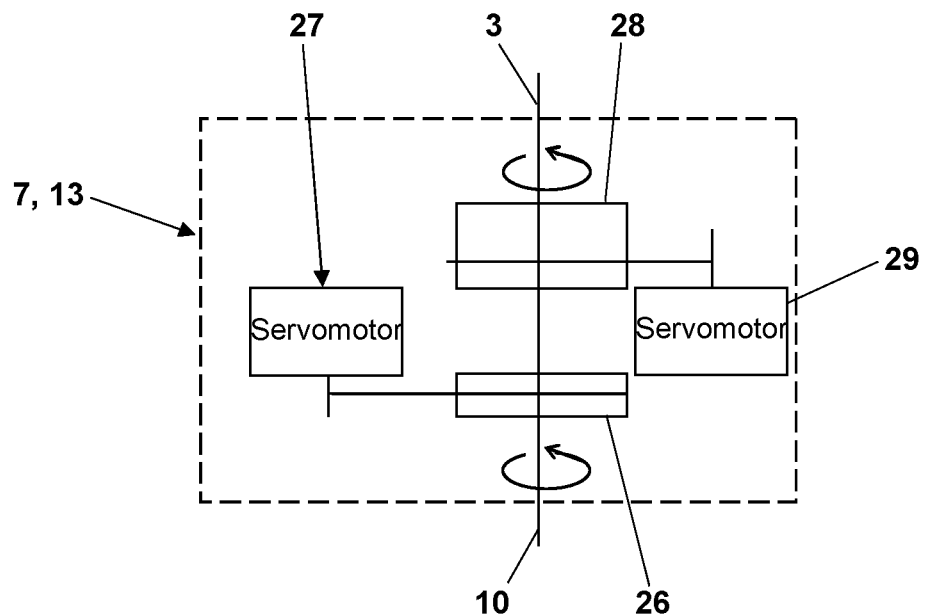
FIGS. 7 to 10 illustrate four possible embodiments of an adaptation device of the laser scanning microscope of the present invention.

FIG. 7 illustrates a further embodiment of the adaptation device 13 connected to the beam shaping elements 7 in a laser scanning microscope 1 of the present invention according to FIGS. 1 to 6. Here, an output side $\lambda/4$ plate 26 and a $\lambda/2$ plate 28 arranged in front of or upstream the $\lambda/4$ are rotated about the optical axis 10 by means of separate servomotors 27 and 29, respectively. The polarization of the beam 3 of fluorescence inhibiting light passing through the beam shaping elements 7 can be adapted by means of the servomotors 27 and 29 such that the beam 3 of fluorescence inhibiting light has the desired circular polarization in the focus after passing through the downstream objective 4, 14 or 24 of the laser scanning microscope 18, which is a precondition for forming the intensity minimum with low residual intensity of the fluorescence inhibiting light. In the embodiment of the adaptation device 13 according to FIG. 7, the servomotor 27 for the $\lambda/4$ plate 26 is only an option, i.e. the $\lambda/4$ plate 26 may also have a fixed rotation position or orientation.

Figure 8:
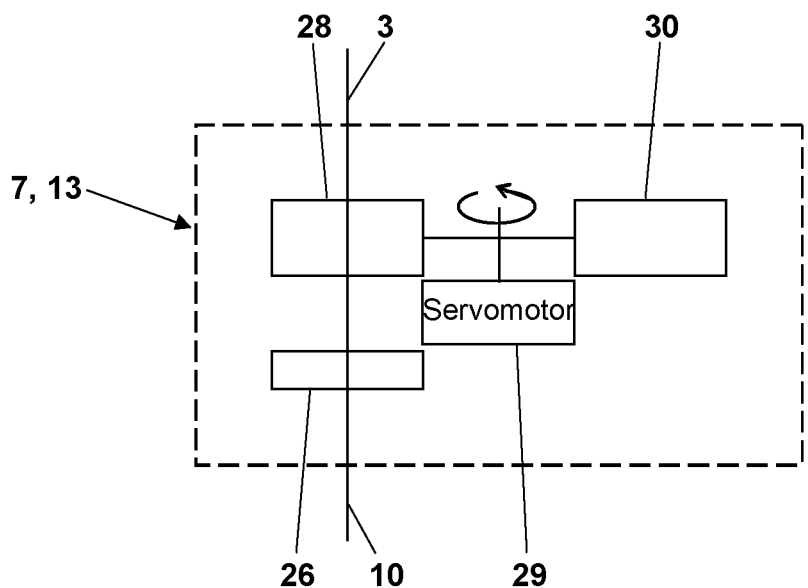

Accordingly, in embodiment of the adaptation device 13 according to FIG. 8, the $\lambda/4$ plate 26 is fixed in rotation, and by means of the servomotor 29, depending on the objective 4, 14 or 24 actually used, the $\lambda/2$ plate 28 having a fixed orientation is exchanged with another $\lambda/2$ plate 30 having another fixed orientation or no $\lambda/2$ plate.

Figure 9:
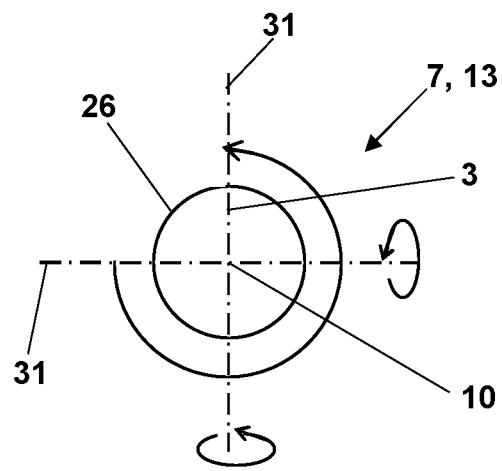

In the embodiment of the adaptation device 13 illustrated in FIG. 9 only the $\lambda/4$ plate 26 is provided. This $\lambda/4$ plate, by means of servomotors not depicted here, is rotated about the optical axis 10 and tilted about two tilting axes 31 which are orthogonal to the optical axis 10. In this way, the desired polarization of the beam 3 of fluorescence inhibiting light in the focus 8 of the objective 4, 14 or 24 can also be set.

Figure 10:
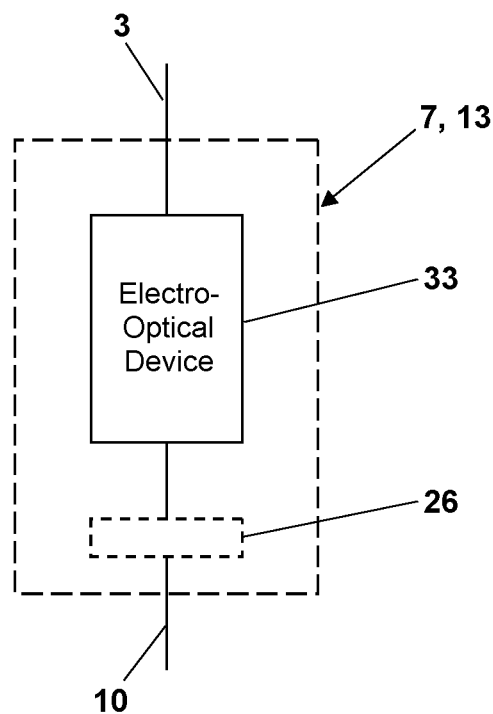

The embodiment of the adaptation device 18 illustrated in FIG. 10 includes an electro-optical device 33 which can be operated for polarization rotation of the beam 3 of fluorescence inhibiting light about the optical axis 10 to compensate a polarization rotation due to different optical elements with different polarization varying properties arranged in the beam path of the beam 3 of fluorescence inhibiting light. Optionally, the adaptation device 13 additionally comprises the λ/4 plate 26 for circularly polarizing the beam 3 of fluorescence inhibiting light. However, the λ/4 plate 26 is, for example, not provided if the beam 3 of fluorescence inhibiting light is linearly polarized by means of a segmented birefringent phase plate with a certain distribution of the polarization directions to form the intensity minimum delimited by intensity maxima in the focus 8 of the objective 4, 14 or 24 due to the polarization of the beam 3 of fluorescence inhibiting light, only.

Many variations and modifications may be made to the preferred embodiments of the invention without departing substantially from the spirit and principles of the invention. All such modifications and variations are intended to be included herein within the scope of the present invention, as defined by the following claims.

We claim:

1. A method of using a high resolution laser scanning microscope having an objective connector and beam shaping elements, the beam shaping elements being configured to shape a beam of fluorescence inhibiting light which is directed into a back aperture of an objective connected to the objective connector at least with regard to its polarization to form an intensity minimum of the fluorescence inhibiting light delimited by intensity maxima of the fluorescence inhibiting light in a focus of the objective, wherein a plurality of optical elements which include the objective and the beam shaping elements are arranged in a beam path of the beam of fluorescence inhibiting light to the focus of the objective, the method including:
    removing or exchanging or altering or adding at least one of the optical elements arranged in the beam path of the beam of fluorescence inhibiting light, and
    compensating a variation of polarization varying properties of the plurality of the optical elements arranged in the beam path of the beam of fluorescence inhibiting light, that is caused by removing or exchanging or altering or adding the at least one optical element, by adapting the beam shaping elements to the variation,
    wherein the step of compensating includes annulling a polarization rotation of the beam of fluorescence inhibiting light, that is caused by removing or exchanging or altering or adding the at least one optical element.

2. The method of claim 1,
    wherein exchanging the optical element includes at least one of exchanging the objective connected to the objective connector with another objective and exchanging a sample substrate made of polarization varying material with another sample substrate of polarization varying material, and
    wherein adapting the beam shaping elements to the variation includes adapting the beam shaping elements to the other objective or the other sample substrate, respectively, such that the variation of the polarization varying properties of the plurality of the optical elements arranged in the beam path of the beam of fluorescence inhibiting light caused by exchanging the objective or the sample substrate, respectively, is compensated.

3. The method of claim 1, wherein adapting the beam shaping elements to the variation includes generating an additional polarization rotation by means of the beam shaping elements.

4. The method of claim 1, wherein adapting the beam shaping elements to the variation includes setting the beam shaping elements to an adjustment predetermined by an identifier of the removed or exchanged or altered or added optical element.

5. The method of claim 4, wherein adapting the beam shaping elements to the variation includes reading in the identifier of the removed or exchanged or altered or added optical element.

6. The method of claim 5, wherein adapting the beam shaping elements to the variation includes reading in the adjustment predetermined by the identifier of the removed or exchanged or altered or added optical element from a database using the identifier.

7. The method of claim 1, wherein adapting the beam shaping elements to the variation includes at least one step selected from
    arranging at least one further beam shaping element in the beam path of the beam of fluorescence inhibiting light,
    removing at least one of the beam shaping elements from the beam path of the beam of fluorescence inhibiting light,
    exchanging at least one of the beam shaping elements arranged in the beam path of the beam of fluorescence inhibiting light, and
    readjusting at least one of the beam shaping elements arranged in the beam path of the beam of fluorescence inhibiting light.

8. The method of claim 7, wherein readjusting the at least one of the beam shaping elements includes at least one step selected from
    rotating at least one of two birefringent optical elements of the beam shaping elements,
    tilting at least one of two birefringent optical elements of the beam shaping elements, and
    adjusting a phase delay of at least one of two birefringent optical elements of the beam shaping elements.

9. The method of claim 1, wherein adapting the beam shaping elements to the variation includes varying an adjustment of the beam shaping elements pursuing at least one goal selected from
    maximizing an intensity of fluorescence light emitted out of the intensity minimum of the fluorescence inhibiting light, and
    minimizing a residual intensity of the fluorescence inhibiting light in the intensity minimum of the fluorescence inhibiting light.

10. The method of claim 1, wherein exchanging the optical element includes replacing the objective connected to the objective connector with another objective, and wherein adapting the beam shaping elements to the variation includes adapting a shape of wavefronts of the beam of fluorescence inhibiting light to the back aperture of the other objective.

11. The method of claim 10, wherein adapting shaping the wavefronts of the beam of fluorescence inhibiting light includes adapting a setting of at least one spatial light modulator or adaptive mirror.

12. A high resolution laser scanning microscope comprising:
    an objective connector and beam shaping elements configured to shape a beam of fluorescence inhibiting light which is directed into a back aperture of an objective connected to the objective connector, at least with regard to its polarization, to form an intensity minimum of the fluorescence inhibiting light delimited by intensity maxima of the fluorescence inhibiting light in a focus of the objective, wherein a plurality of optical elements including the objective and the beam shaping elements are arranged in a beam path of the beam of fluorescence inhibiting light to the focus of the objective, wherein the laser scanning microscope further comprises an adaptation device operatively connected to the beam shaping elements and configured to compensate a variation of polarization varying properties of the plurality of the optical elements arranged in the beam path of the beam of fluorescence inhibiting light, the variation coming along with removing or exchanging or altering or adding the at least one the optical element, wherein the adaptation device is configured to annul a polarization rotation of the beam of fluorescence inhibiting light, that is caused by removing or exchanging or altering or adding the at least one optical element.

13. The laser scanning microscope of claim 12, further comprising at least one of a read in device and input device for an identifier of a removed or exchanged or altered or added optical element.

14. The laser scanning microscope of claim 12, wherein the read in device is located at the objective connector.

15. The laser scanning microscope of claim 12, wherein the adaptation device is configured to set the beam shaping elements to an adjustment predetermined by the identifier.

16. The laser scanning microscope of claim 12, wherein the beam shaping elements include at least two birefringent optical elements, wherein at least one of the two birefringent optical elements is selected from birefringent optical elements configured to be rotated or tilted about at least one axis by the adaptation device, birefringent optical elements configured to be rotated or tilted about two orthogonal space axes by the adaptation device, birefringent optical elements configured to be electrically rotated or tilted by the adaptation device, and birefringent optical elements configured to be rotated or tilted by a motor of the adaptation device.

17. The laser scanning microscope of claim 12, wherein the beam shaping elements include at least two birefringent optical elements, wherein at least one of the two birefringent optical elements is selected from birefringent optical elements configured to be adjusted with regard to their phase delay by the adaptation device, and birefringent optical elements configured to be electrically adjusted with regard to their phase delay by the adaptation device.

18. The laser scanning microscope of claim 12, wherein the birefringent optical element is selected from one of the following groups:

waveplates, $\lambda/2$ and $\lambda/4$ plates, liquid crystal devices (LCD) and liquid crystal polymers (LCP) and electro-optical (EO) elements.

19. The laser scanning microscope of claim 12, wherein the beam shaping elements include an optically active substance.

20. The laser scanning microscope of claim 12, wherein the beam shaping elements include at least one beam wavefront shaping element configured to shape wavefronts of the beam of fluorescence inhibiting light and selected from a spatial light modulator and an adaptive mirror, wherein the adaptation device is configured to operate the at least one beam wavefront shaping element such as to adapt a shape of the wavefronts of the beam of fluorescence inhibiting light to the back aperture of the objective presently connected to the objective connector.

* * * * *